(12) United States Patent
Witte et al.

(10) Patent No.: US 10,088,762 B2
(45) Date of Patent: Oct. 2, 2018

(54) INSPECTION APPARATUS AND METHOD

(71) Applicant: ASML Netherlands B.V., Veldhoven (NL)

(72) Inventors: Stefan Michiel Witte, Hoofddorp (NL); Kjeld Sijbrand Eduard Eikema, Hoofddorp (NL)

(73) Assignee: ASML Netherlands B.V., Veldhoven (NL)

( * ) Notice: Subject to any disclaimer, the term of this patent is extended or adjusted under 35 U.S.C. 154(b) by 20 days.

(21) Appl. No.: 15/381,980

(22) Filed: Dec. 16, 2016

(65) Prior Publication Data
US 2017/0176879 A1   Jun. 22, 2017

(30) Foreign Application Priority Data

Dec. 18, 2015  (EP) .................................... 15201162

(51) Int. Cl.
G01N 23/2055 (2018.01)
G03F 9/00 (2006.01)
(Continued)

(52) U.S. Cl.
CPC .......... *G03F 9/7042* (2013.01); *G01B 15/00* (2013.01); *G01N 23/2055* (2013.01); *G03F 7/70625* (2013.01); *H05G 2/008* (2013.01)

(58) Field of Classification Search
CPC .... G01B 15/00; H05G 2/008; G01N 23/2005; G01N 23/2055; G03F 7/70625; G03F 9/7042

See application file for complete search history.

(56) References Cited

U.S. PATENT DOCUMENTS 6,623,893 B1   9/2003 Levinson et al.
7,548,575 B1   6/2009 Jackson et al.
(Continued)

FOREIGN PATENT DOCUMENTS

JP    H1-319727        12/1989
WO    WO 2017/016903 A1   2/2017

OTHER PUBLICATIONS

Seaberg et al., "Ultrahigh 22 nm resolution coherent diffractive imaging using a desktop 13 nm high harmonic source," Optical Society of America, Optics Express, vol. 19, No. 23, Nov. 7, 2011; pp. 22470-22479.

(Continued)

*Primary Examiner* — David Porta
*Assistant Examiner* — Faye Boosalis
(74) *Attorney, Agent, or Firm* — Sterne, Kessler, Goldstein & Fox P.L.L.C.

(57) ABSTRACT

A lithographic apparatus is a machine that applies a desired pattern onto a substrate, usually onto a target portion of the substrate. A lithographic apparatus can be used, for example, in the manufacture of integrated circuits (ICs). The lithographic apparatus has an inspection apparatus with an EUV radiation source. The radiation source emits a radiation beam that includes coherent radiation of a specific wavelength. The beam propagates to illumination optical system, which focuses the radiation beam into a focused beam of illuminating radiation. The illumination optical system illuminates a three-dimensional product structure on the substrate, which scatters the illuminating radiation. On the surface of a detector, the radiation scattered by the product structure forms a diffraction pattern that is used to reconstruct data describing the three-dimensional product structure.

12 Claims, 8 Drawing Sheets

(51) Int. Cl.
*G01B 15/00* (2006.01)
*H05G 2/00* (2006.01)
*G03F 7/20* (2006.01)

(56) References Cited

U.S. PATENT DOCUMENTS

| | | | |
|---|---|---|---|
| 7,791,732 B2* | 9/2010 | Den Boef | G03F 7/70341 356/456 |
| 2005/0286599 A1 | 12/2005 | Rafac et al. | |
| 2006/0066855 A1 | 3/2006 | Boef et al. | |
| 2008/0144671 A1 | 6/2008 | Ershov et al. | |
| 2008/0212075 A1 | 9/2008 | Paulus et al. | |
| 2011/0102753 A1 | 5/2011 | Van De Kerkhof et al. | |
| 2012/0044470 A1 | 2/2012 | Smilde et al. | |

OTHER PUBLICATIONS

Claus et al., "Dual wavelength optical metrology using ptychography," Journal of Optics, vol. 15, No. 3, 2013; pp. 1-7.

Bao et al., "Phase retrieval using multiple illumination wavelengths," Optical Society of America, Optics Letters, vol. 33, No. 4, Feb. 15, 2008; pp. 309-311.

Bao et al., "Lensless phase microscopy using phase retrieval with multiple illumination wavelengths," Optical Society of America, Applied Optics, vol. 51, No. 22, Aug. 1, 2012; pp. 5486-5494.

International Search Report and Written Opinion of the International Searching Authority directed to related International Patent Application No. PCT/EP2016/079770, dated Apr. 25, 2017; 14 pages.

English-language abstract for Japanese Patent Publication No. H1-319727, published Dec. 26, 1989; 2 pages.

Witte et al., "Lensless diffractive imaging with ultra-broadband table-top sources: from infrared to extreme-ultraviolet wavelengths," Light: Science & Applications 3, e163, 2014; pp. 1-8.

Huang et al., "Optical Coherence Tomography," Science, New Series, vol. 254, No. 5035, Nov. 22, 1991; pp. 1178-1181.

Zhang, B., "EUV Microscopy with a Tabletop High Harmonic Generation Source: Generalizing Coherent Diffractive Imaging to Extended Samples in Transmission, Reflection, and Hyperspectral Modalities," University of Science and Technology of China, Department of Physics, 2007; 119 pages.

Lee et al., "A novel concept for actinic EUV mask review tool using a scanning lensless imaging method at the Swiss Light Source," Extreme Ultraviolet (EUV) Lithography V, SPIE, vol. 9048, No. 904811, 2014; pp. 1-7.

Kuhn et al., "Submicrometer tomography of cells by multiple-wavelength digital holographic microscopy in reflection," Optic Letters, vol. 34, No. 5, Mar. 1, 2009; pp. 653-655.

* cited by examiner

INSPECTION APPARATUS AND METHOD

BACKGROUND

Field of the Invention

The present invention relates to inspection apparatus and methods usable, for example, to perform metrology in the manufacture of devices by lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

Examples of known scatterometers often rely on provision of dedicated metrology targets. For example, a method may require a target in the form of a simple grating that is large enough that a measurement beam generates a spot that is smaller than the grating (i.e., the grating is underfilled). In so-called reconstruction methods, properties of the grating can be calculated by simulating interaction of scattered radiation with a mathematical model of the target structure. Parameters of the model are adjusted until the simulated interaction produces a diffraction pattern similar to that observed from the real target.

In addition to measurement of feature shapes by reconstruction, diffraction based overlay can be measured using such apparatus, as described in published patent application US2006066855A1. Diffraction-based overlay metrology using dark-field imaging of the diffraction orders enables overlay measurements on smaller targets. These targets can be smaller than the illumination spot and may be surrounded by product structures on a wafer. Examples of dark field imaging metrology can be found in numerous published patent applications, such as for example US2011102753A1 and US20120044470A. Multiple gratings can be measured in one image, using a composite grating target. The known scatterometers tend to use light in the visible or near-IR wave range, which requires the grating to be much coarser than the actual product structures whose properties are actually of interest. Such product features may be defined using deep ultraviolet (DUV) or extreme ultraviolet (EUV) radiation having far shorter wavelengths. Unfortunately, such wavelengths are not normally available or usable for metrology. Product structures made for example of amorphous carbon may be opaque to radiation of shorter wavelength.

On the other hand, the dimensions of modern product structures are so small that they cannot be imaged by optical metrology techniques. Small features include for example those formed by multiple patterning processes, and/or pitch-multiplication. Hence, targets used for high-volume metrology often use features that are much larger than the products whose overlay errors or critical dimensions are the property of interest. The measurement results are only indirectly related to the dimensions of the real product structures, and may be inaccurate because the metrology target does not suffer the same distortions under optical projection in the lithographic apparatus, and/or different processing in other steps of the manufacturing process. While scanning electron microscopy (SEM) is able to resolve these modern product structures directly, SEM is much more time consuming than optical measurements. Other techniques, such as measuring electrical properties using contact pads is also known, but it provides only indirect evidence of the true product structure.

The inventor has considered whether the techniques of coherent diffraction imaging (CDI), combined with radiation of wavelength comparable with the product structures of interest, might be applied to measure properties of device structures. CDI is also known as lensless imaging, because there is no need for physical lenses or mirrors to focus an image of an object. The desired image is calculated synthetically from a captured light field.

Using lensless imaging to retrieving images of two-dimensional structures has been demonstrated. For example, two-dimensional structures have been obtained for both transmission and reflection geometries, achieving 22 nm transverse spatial resolution ("Lensless diffractive imagine with ultra-broadband table-top sources: from infrared to extreme-ultraviolet wavelengths" M. D. Seaberg et al., Optics Express 19, 22470 (2011)). Additionally, it has been demonstrated that it is possible to image through thin metal layers using lensless imaging at extreme ultraviolet (EUV) wavelengths (S. Witte et al., Light: Science & Applications, e163 (2014)).

However, using these methods, it is not possible to obtain information regarding the three-dimensional properties, in particular depth information, of a given structure. In effect, it is not possible to obtain information regarding patterned layers inside a structure. Given that product structures typically comprise several patterned layers, this is a drawback. Furthermore, existing inspection methods, such as SEM, also do not provide any depth information regarding multi-layer structures.

SUMMARY OF THE INVENTION

The present invention aims to provide an alternative inspection apparatus and method for performing measurements of the type described above.

The inventors have determined that it is possible to retrieve depth information regarding a three-dimensional, or multi-layer, product structure from the amplitude and phase of a reflected frequency spectrum. In the following, the terms "three-dimensional product structure", "multi-layer product structure" and "product structure" are used interchangeably to describe product structures that consist of a plurality of patterned layers. This approach is known as optical coherence tomography (OCT), and is in use for depth imaging in other fields (such as medical imaging). In OCT, the phase of a measured frequency spectrum is retrieved through interferometry with a known reference wave, as is described in detail in the paper "Optical Coherence Tomography" Huang et al., Science 254, 1178 (1991).

Conventionally in OCT, the transverse structure of an object to be imaged is retrieved using a lens-based optical system. Spectral information is obtained by spectrometry using a broadband light source, or by using frequency scanning using a narrowband light source.

The inventors have realized that it is possible to perform three-dimensional lensless imaging at EUV wavelengths in a similar fashion, by replacing the interferometric detection of traditional OCT by the use of a numerical phase retrieval algorithm similar to what is used to retrieve transverse spatial information.

According to a first aspect of the present invention, there is provided method of obtaining data describing a three-dimensional product structure, the method comprising the steps of:

(a) illuminating the three-dimensional product structure with illuminating radiation, the illuminating radiation having at least one controllable characteristic;

(b) capturing a plurality of diffraction patterns formed by said radiation after scattering by the three-dimensional product structure, each diffraction pattern being formed by illuminating radiation having a specific value of the at least one controllable characteristic; and (c) reconstructing data describing the three-dimensional product structure based on the captured plurality of diffraction patterns.

According to a second aspect of the present invention, there is provided inspection apparatus, comprising:

an illumination optical system operable to illuminate a three-dimensional product structure on a substrate with illuminating radiation, the illuminating radiation having at least one controllable characteristic;

a detector operable to capture a plurality of diffraction patterns formed by said radiation after scattering by the three-dimensional product structure, each diffraction pattern being formed by illuminating radiation having a specific value of the at least one controllable characteristic; and a processing unit operable to reconstruct data describing the three-dimensional product structure based on the captured plurality of diffraction patterns.

Such a method and apparatus can be used to perform so-called "lensless" imaging. This avoids the difficulties associated with providing imaging optics for the shorter wavelengths. The image obtained and used to measure properties of the structure may be called a "synthetic image" because it never existed in the physical world: it exists only as data and is obtained by computation from data representing the scattered radiation field.

The invention yet further provides a method of manufacturing devices wherein three-dimensional product structures are formed on a series of substrates by a lithographic process, wherein properties of the product structures on one or more processed substrates are measured by a method according to the invention as set forth above, and wherein the measured properties are used to adjust parameters of the lithographic process for the processing of further substrates.

The invention yet further provides a computer program product containing one or more sequences of machine-readable instructions for implementing reconstructions steps in a method according to the invention as set forth above.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
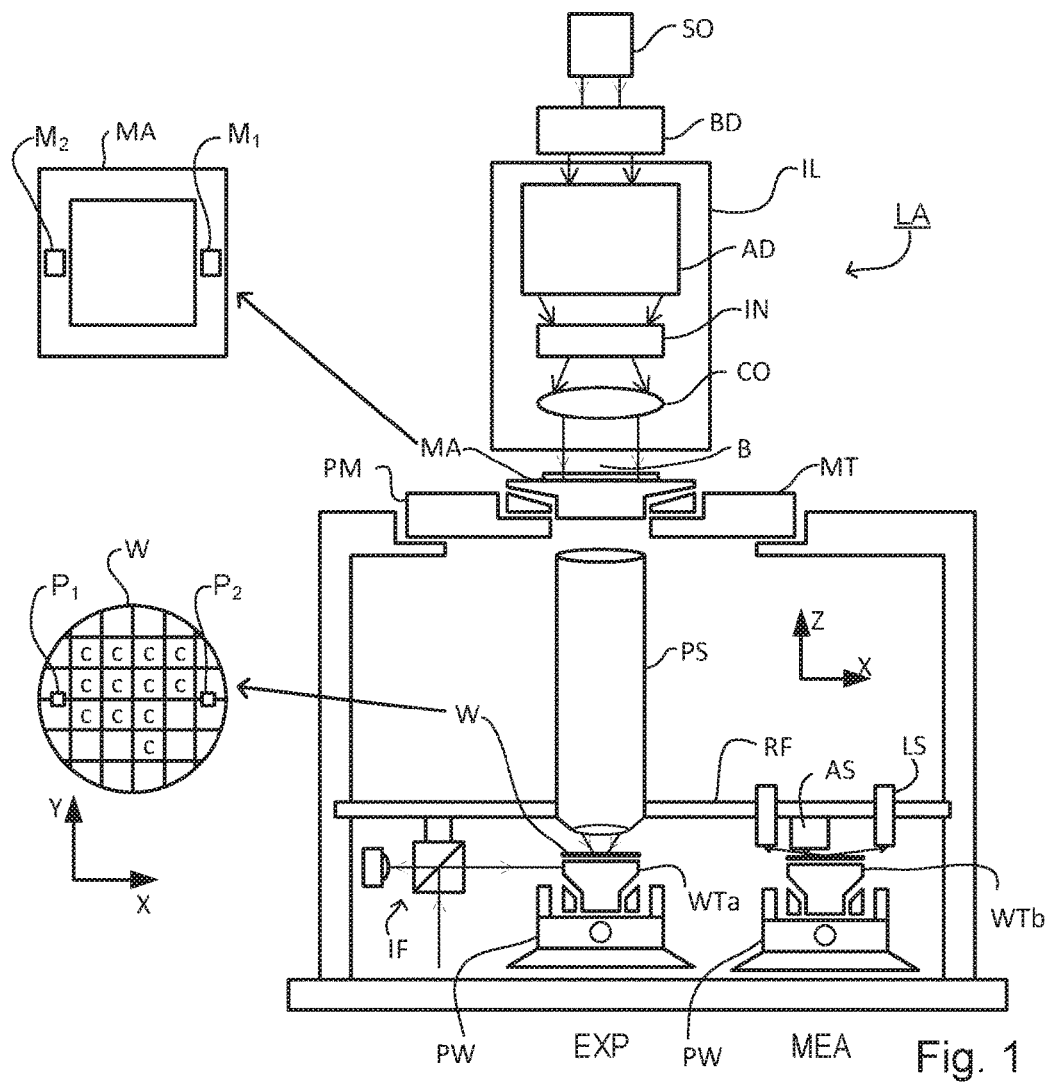
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation. For example, in an apparatus using extreme ultraviolet (EUV) radiation, reflective optical components will normally be used.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers, is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
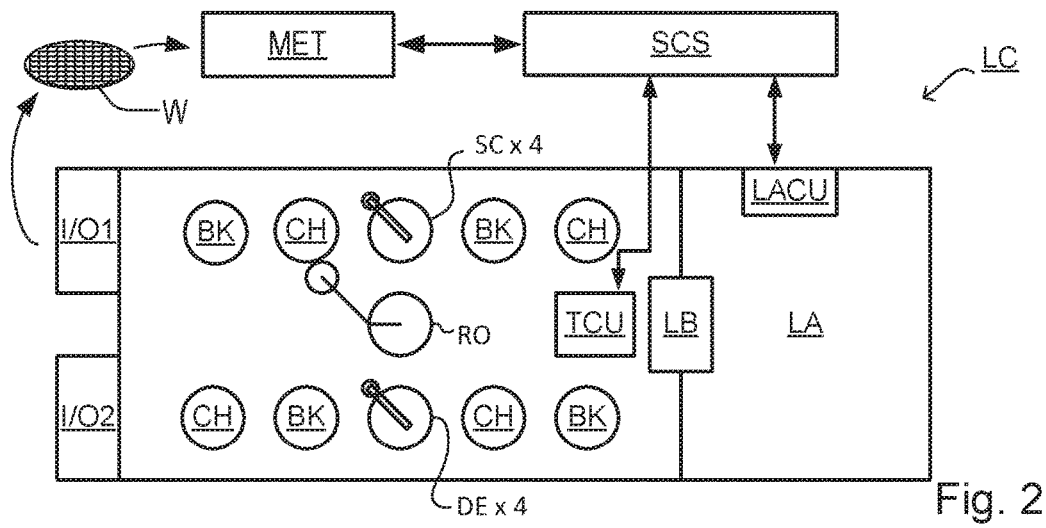
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it may be desirable that the inspection apparatus measure properties in the exposed resist layer immediately after the exposure. However, not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

The metrology step with metrology system MET can also be done after the resist pattern has been etched into a product layer. The latter possibility limits the possibilities for rework of faulty substrates but may provide additional information about the performance of the manufacturing process as a whole.

Figure 3:
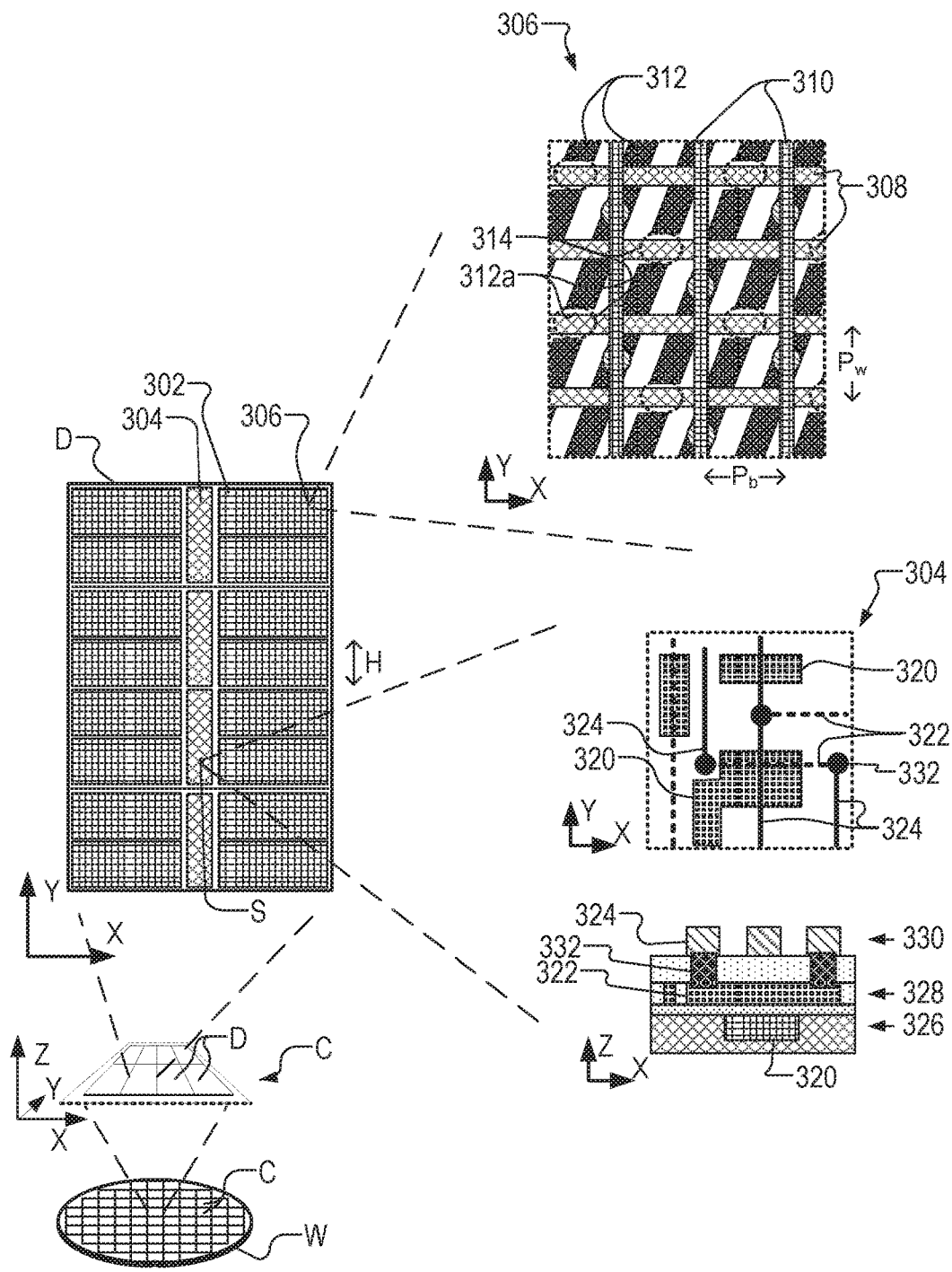
FIG. 3 illustrates schematically a three-dimensional product structure having a nominal form in periodic areas and non-periodic areas.

FIG. 3 illustrates characteristics of a three-dimensional product structure that might be subject to measurement by the metrology system MET. It will be assumed that the product structures have been formed by optical lithography, using a system of the type described above with respect to FIGS. 1 and 2. The present disclosure is applicable to measurement of microscopic structures formed by any technique, however, not only optical lithography. A substrate W has product structure formed in target portions C, which may correspond for example to fields of the lithographic apparatus. Within each field a number of device areas D may be defined, each corresponding for example to a separate integrated circuit die.

Within each device area D, product structures formed by lithographic processing are arranged to form functional electronic components. The product illustrated may, for example, comprise a DRAM memory chip. It may have dimension of a few millimeters in each direction. The product comprises a number of memory array areas 302, and a number of logic areas 304. Within the memory array areas 302, sub-areas 306 comprise individual arrays of memory cell structures. Within these sub-areas, the product structures may be periodic. Using known reconstruction techniques, this periodicity can be exploited for measurement purpose. On the other hand, in the logic areas 304, the structure may comprise stub-structures arranged in a non-periodic fashion. Conventional reconstruction techniques are not suited to such structures, and the present disclosure applies lensless imaging particularly to enable metrology in these non-periodic areas.

On the right hand side of FIG. 3, there is shown a small portion of a periodic product structure 306 (plan view only) and a small portion of non-periodic structure 304 (plan and cross-section). Again, the periodic structure could be that of a DRAM memory cell array, but is used only for the sake of example. In the example structure, conductors forming word lines 308 and bit lines 310 extend in X and Y directions throughout the periodic structure. The pitch of the word lines is marked Pw and the pitch of the bit lines is marked Pb. Each of these pitches may be a few tens of nanometers, for example. An array of active areas 312 is formed beneath the word lines and bit lines, with a slanted orientation. The active areas are formed from an array of line features, but cut at locations 312a to be divided longitudinally. The cuts may be made for example by a lithographic step using a cut mask, shown in dotted outline at 314. The process of forming the active areas 312 is thus an example of a multiple patterning process. Bit line contacts 316 are formed at locations to connect each bit line 310 with the active areas 312 below it. The skilled person will appreciate that the different types of features shown in the example product structure are separated in the Z direction, being formed in successive layers during a lithographic manufacturing process.

Also shown on the right hand side in FIG. 3 is a portion of non-periodic product structure 304, which may be part of the logic area of the DRAM product, just by way of example. This structure may comprise for example active areas 320 and conductors 322, 324. The conductors are shown only schematically in the plan view. As can be seen in the cross-section, active areas 320 are formed in a bottom layer 326, conductors 322 are formed in an intermediate layer 328 and conductors 324 are formed in a top layer 330. The term "top layer" refers to the state of manufacturing shown in the diagram, which may or may not be the top layer in a finished product. Contacts 332 are formed to interconnect conductors 322 and 324 at desired points.

Final performance of manufactured device depends critically on the accuracy of positioning and dimensioning of the various features of the product structure through lithography and other processing steps. While FIG. 3 shows the ideal or nominal product structures 304 and 306, a product structure made by a real, imperfect, lithographic process will produce a slightly different structure. An imperfect product structure will be illustrated below, with reference to FIG. 6.

Overlay error may cause cutting, contact or other modification to occur imperfectly, or in a wrong place. Dimensional (CD) errors may cause cuts be too large, or too small (in an extreme case, cutting a neighboring line by mistake, or failing to cut the intended grid line completely). Performance of devices can be influenced by other parameters of lithographic performance, such as CD uniformity (CDU), line edge roughness (LER) and the like. For reasons mentioned above, it is desirable to perform metrology directly on such structures to determine the performance of the lithographic process for CD, overlay and the like.

For metrology to be performed on a section of product structure in a logic area 304, a spot S of radiation is indicated. The spot diameter may be for example 10 μm or smaller, using the example DRAM structure mentioned above.

Figure 4:
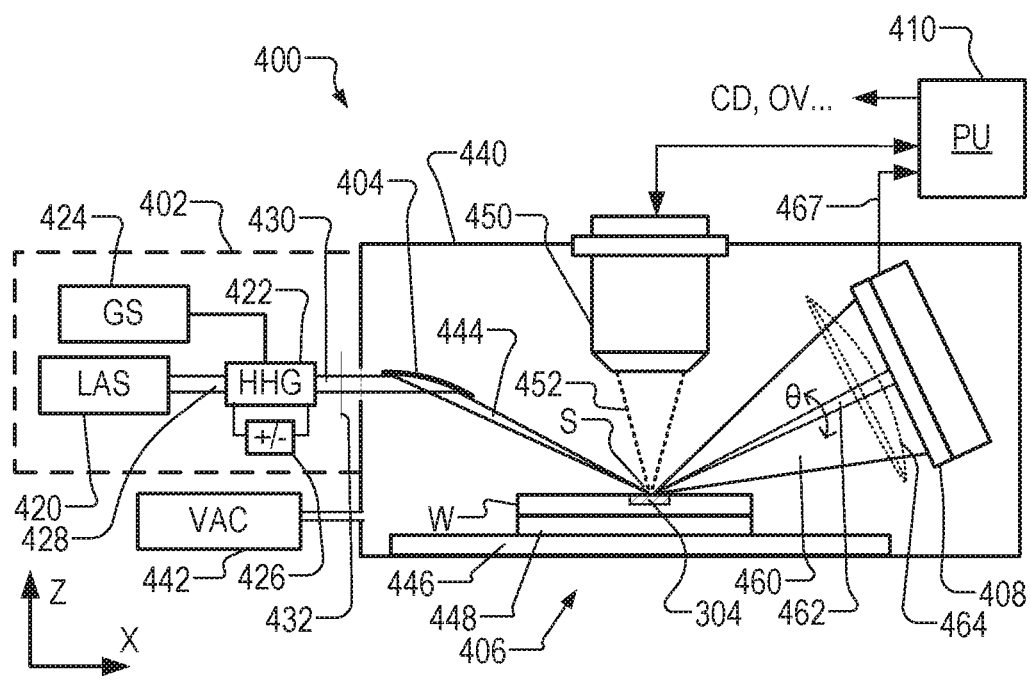
FIG. 4 illustrates schematically an inspection apparatus for use in measuring the three-dimensional product structure of FIG. 3.

FIG. 4 illustrates in schematic form an inspection apparatus 400 for use in the metrology system MET of FIG. 2. This apparatus is for implementing so-called lensless imaging in wavelengths in the extreme UV (EUV) and soft x-ray (SXR) ranges. For example the radiation used may be at a selected wavelength or wavelengths less than 50 nm, optionally less than 20 nm, or even less than 5 nm or less than 2 nm.

Inspection apparatus 400 comprises an EUV radiation source 402, illumination optical system 404, substrate support 406, detector 408 and processor 410. Source 402 comprises for example a generator of EUV radiation based on high harmonic generation (HHG) techniques. Such sources are available for example from KMLabs, Boulder Colorado, USA (http://www.kmlabs.com/). Main components of the radiation source are a pump laser 420 and an HHG gas cell 422. A gas supply 424 supplies suitable gas to the gas cell, where it is optionally ionized by electric source 426. The pump laser may be for example a fiber-based laser with an optical amplifier, producing pulses of infrared radiation lasting less than 1 ns (1 nanosecond) per pulse, with a pulse repetition rate up to several megahertz, as required. Typical pulse durations may be in the sub-picosecond range. The wavelength may be for example in the region of 1 μm (1 micron). The laser pulses are delivered as a first beam of radiation 428 to the HHG gas cell 422, where a portion of the radiation is converted to higher frequencies. The filtered radiation beam 430 includes coherent radiation of the desired EUV wavelength or wavelengths. The radiation for the purpose of coherent diffraction imaging should be spatially coherent but it may contain multiple wavelengths. If the radiation is also monochromatic the lensless imaging calculations may be simplified, but it is easier with HHG to produce radiation with several wavelengths. These are matters of design choice, and may even be selectable options within the same apparatus. One or more filtering devices 432 may be provided. For example a filter such as a thin membrane of Aluminum (Al) may serve to cut the fundamental IR radiation from passing further into the inspection apparatus. A grating may be provided to select one or more specific harmonic wavelengths from among those generated in the gas cell. Some or all of the radiation path may be contained within a vacuum environment, bearing in mind that the desired EUV radiation is absorbed when traveling in air. The various components of radiation source 402 and illumination optics 404 can be adjustable to implement different metrology 'recipes' within the same apparatus. For example different wavelengths and/or polarization can be made selectable.

For high-volume manufacturing applications, selection of a suitable source will be guided by cost and hardware size, not only by theoretical ability, and HHG sources are selected as the example here. Other types of sources are also available or under development that may be applied in principle. Examples are synchrotron sources, FEL (free electron laser) sources and filtered plasma-based sources. T. Depending on the materials of the structure under inspection, different wavelengths may offer a desired level of penetration into lower layers, for imaging of buried structures. For example, wavelengths above 4 or 5 nm may be used. Wavelengths above 12 nm may be used, as these show stronger penetration specifically through silicon material and are available from bright, compact HHG sources. For example, wavelengths in the range 12 to 16 nm may be used. Alternatively or in addition, shorter wavelengths may be used that also exhibit good penetration. For example, wavelengths shorter than 2 nm may be used, as and when a practical source becomes available. Wavelengths in ranges above 0.1 nm and below 50 nm might therefore be considered, including for example the range 1 to 2 nm. The apparatus may be a stand-alone device or incorporated in either the lithographic apparatus LA, or the lithographic cell LC. It can also be integrated in other apparatuses of the lithographic manufacturing facility, such as an etching tool. The apparatus may of course be used in conjunction with other apparatuses such as scatterometers and SEM apparatus, as part of a larger metrology system.

From the radiation source 402, the filtered radiation beam 430 enters an inspection chamber 440 where the substrate W including a product structure is held for inspection by substrate support 406. The product structure is labeled 304, indicating that he apparatus is particularly adapted for metrology on non-periodic structures, such as the logic area 304 of the product shown in FIG. 3. The atmosphere within inspection chamber 440 is maintained near vacuum by vacuum pump 442, so that EUV radiation can pass without undue attenuation through the atmosphere. The Illumination optics 404 has the function of focusing the filtered radiation beam 430 into a focused beam of illuminating radiation 444, and may comprise for example a two-dimensionally curved mirror, or a series of one-dimensionally curved mirrors. The focusing is performed to achieve a round spot roughly 10 μm in diameter, when projected onto the product structure. Substrate support 406 comprises for example an X-Y translation stage 446 and a rotation stage 448, by which any part of the substrate W can be brought to the focal point of the beam of illuminating radiation 444 in a desired orientation. Thus the radiation spot S is formed on the structure of interest. Tilting of the substrate in one or more dimensions may also be provided. To aid the alignment and focusing of the spot S with desired product structures, auxiliary optics 450 uses auxiliary radiation 452 under control of processor.

Detector 408 captured radiation 460 that is scattered by the product structure 304 over a range of angles θ in two dimensions. A specular ray 462 represents a "straight through" portion of the radiation. This specular ray may optionally be blocked by a stop (not shown), or pass through an aperture in detector 408. In a practical implementation, images with an without the central stop may be taken and combined to obtain a high dynamic range (HDR) image of a diffraction pattern. The range of angles of diffraction can be plotted on a notional sphere 464, known in the art as the Ewald sphere, while the surface of the detector 408 will more conveniently be flat. Detector 408 may be for example a CCD image detector comprising an array of pixels.

Figure 5:
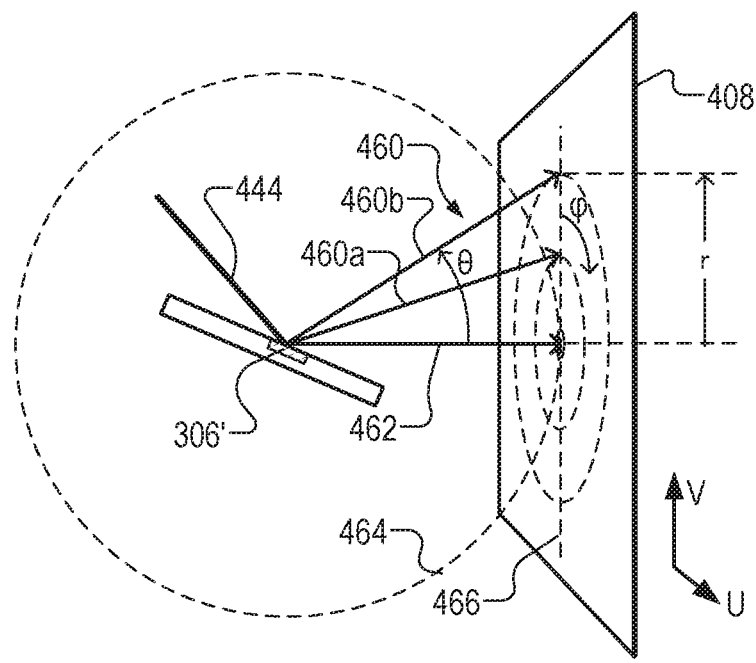
FIG. 5 (not to scale) illustrates the mapping of diffraction angles to pixels on a planar detector in the apparatus for FIG. 4.

FIG. 5 (not to scale) illustrates the mapping of diffraction angles (and consequently points on the Ewald sphere 464) to pixels on a planar detector 408. The dimensions of the pixel array are labeled U, V in a pseudo-perspective representation. The diffracted radiation 460 is deflected by a sample product structure at a point that defines the center of the Ewald sphere 464. Two rays 460a and 460b of the diffracted radiation are scattered by the product structure, with respective angles θ relative to the specular ray 462. Each ray 460a, 460b passes through a point on the (notional) Ewald sphere impinges on a particular point in the (actual) U-V plane of detector 408, where it is detected by a corresponding pixel detector. Knowing the geometry of the apparatus within the inspection chamber, processor 410 is able to map pixel positions in an image captured by detector 408 to angular positions on the Ewald sphere 462. For convenience, the specular portion 462 of the reflected radiation is aligned with the horizontal direction in the diagram, and a direction normal to the plane of detector 408, but any coordinate system can be chosen. Thus a radial distance r on detector 408 can be mapped to an angle θ. A second angular coordinate φ represents deflection out of the plane of the diagram, and can be mapped also from the position on the detector. Only rays with φ=0 are shown in this illustration, corresponding to pixels on a line 466 on the detector.

Returning to FIG. 4, pixel data 467 is transferred from detector 408 to processor 410. Using lensless imaging, a 3-D image (model) of the target can be reconstructed from the diffraction pattern captured on the image detector. From the reconstructed image, measurements of deviations such as overlay and CD are calculated by processor 410 and delivered to the operator and control systems of the lithographic manufacturing facility. Note that the processor 410 could in principle be remote from the optical hardware and inspection chamber. Functions of the processor could be divided between local and remote processing units, without departing from the principles disclosed herein. For example, a local processor may control the apparatus to capture images from one or more product structures on one or more substrates, while a remote processor processes the pixel data to obtain measurements of the structure. The same processor or yet another processor could form part of the supervisory control system SCS or lithographic apparatus controller LACU and use the measurements to improve performance on future substrates.

Figure 6:
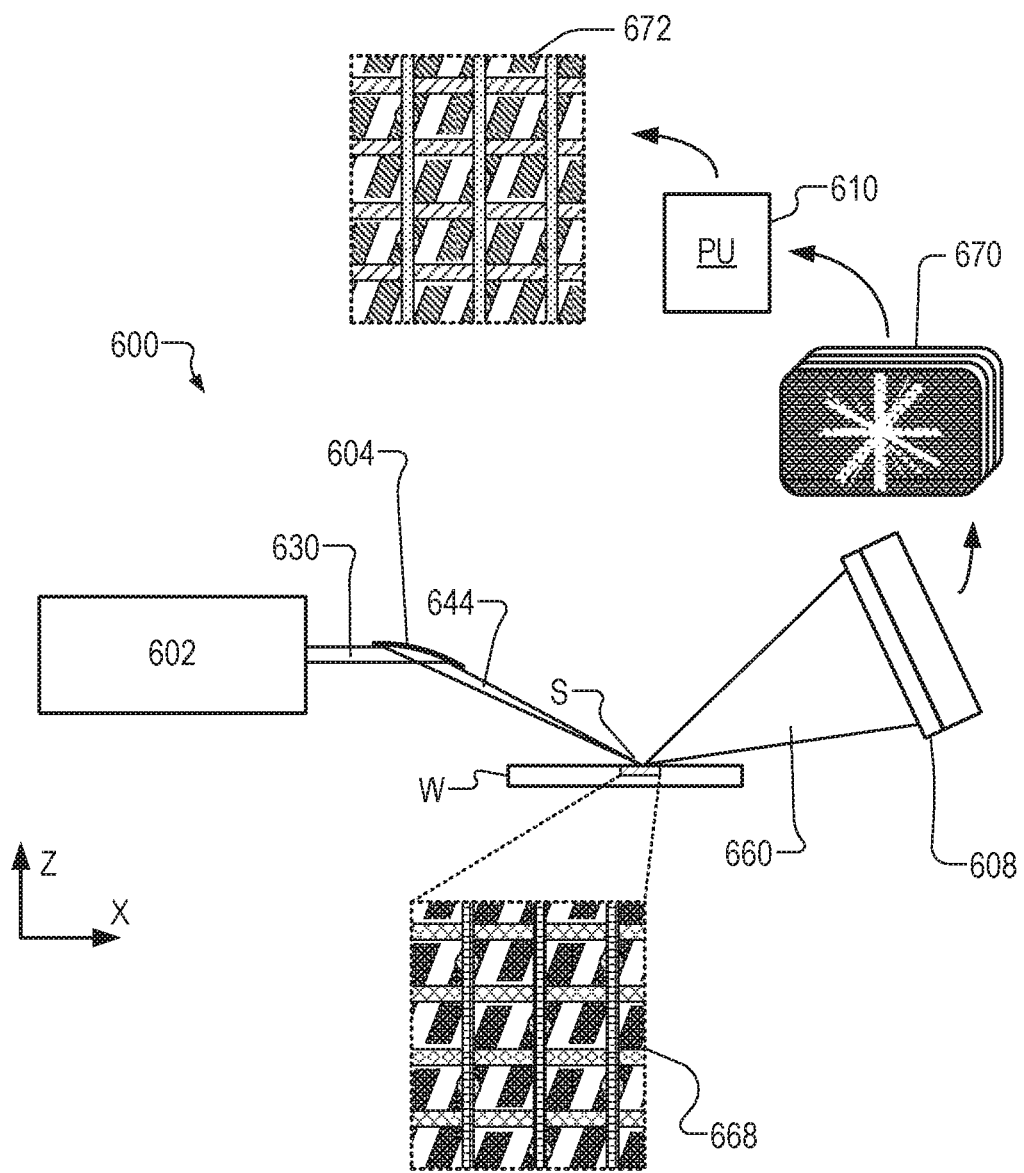
FIG. 6 illustrates schematically an inspection apparatus for obtaining data describing a three-dimensional product structure according to an embodiment of the invention.
Figure 7:
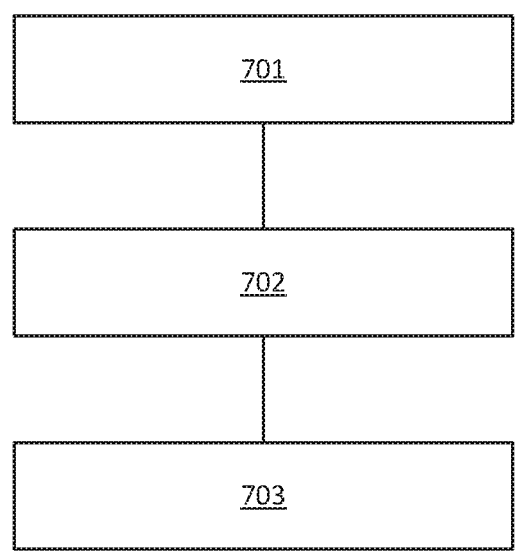
FIG. 7 illustrates a method for obtaining data describing a three-dimensional product structure using, for example, the apparatus of FIG. 6.

An exemplary apparatus and corresponding method for obtaining data describing a three-dimensional product structure will now be described with reference to FIGS. 6 and 7. In this example, the inspection apparatus shown in FIG. 6 is used to perform the steps of the method. For ease of comparison with the inspection apparatus of FIG. 4, the parts of inspection apparatus 600 are labeled with reference signs similar to those used in FIG. 4, but with prefix "6" rather than "4". It will be appreciated that, for purposes of clarity, some of the features or elements of the inspection apparatus 400 of FIG. 4 are not described in the following, but that such features or elements may nevertheless be present Inspection apparatus 600 comprises an EUV radiation source 602, which emits a radiation beam 630. The radiation beam includes coherent radiation of a desired EUV wavelength or wavelengths, and may be filtered by an appropriate filtering mechanism as described above. The radiation beam may have at least one controllable characteristic. The beam propagates to illumination optical system 604, which focuses the radiation beam into a focused beam of illuminating radiation 644. The illumination optical system may comprise, for example, a two-dimensionally curved mirror or a series of one-dimensionally curved mirrors. In a first step 701, the illumination optical system illuminates a three-dimensional product structure 668 by focusing the radiation beam into a substantially round spot S on the substrate W. In the present example, the product structure 668 is a periodic product structure, for example a DRAM memory cell array (substantially identical to the periodic structure 306 of FIG. 3), although it will of course be appreciated that the exemplary method is applicable to any type of product structure (such as structure 304 from FIG. 3).

In a second step 702, a detector 608 captures radiation 660 that is scattered by the three-dimensional product structure 668. On the surface of the detector, the radiation scattered by the product structure forms a so-called diffraction pattern. In the present example, a plurality of diffraction patterns 670 are captured by the detector, each diffraction pattern being formed by radiation having a specific value of the at least one controllable characteristic of the radiation beam 630. The captured diffraction patterns are subsequently transmitted to a processing unit 610.

In a third step 703, the recorded diffraction patterns 670 are used to reconstruct data representing the three-dimensional product structure 672. In the present example, the reconstruction is performed by using a phase retrieval algorithm. In one example, phase retrieval is performed individually on each diffraction pattern of the plurality of diffraction patterns. In another example, phase retrieval is performed on all of the recorded diffraction patterns simultaneously by using an integrated phase retrieval algorithm.

It will be appreciated that the inspection apparatus 600 may comprise further optical components in addition to those described above. For example, additional imaging optics, including but not limited to Fresnel zone plates or curved/multilayer mirrors, may be used if necessary (for example to improve certain functional aspects of the apparatus).

Further, it will be appreciated that the above method may comprise additional method steps. In one example, the method may additionally comprise a step of reconstructing a three-dimensional image of the product structure based on the data.

Additionally, it will be appreciated that whilst a particular lensless imaging method is described in the above (and indeed in the following), this should be considered exemplary only. Other lensless imaging methods could equally well be used as a basis for carrying out the above-described method of obtaining a three-dimensional image, including but not limited to Gerchberg-Saxon methods, multi-wavelength Fresnel diffraction, multi-height Fresnel diffraction or ptychography.

Furthermore, it will be appreciated that, while the above-described apparatus and method utilize radiation at EUV wavelengths, the above-described methodology is in essence wavelength independent. In other terms, the above method may be applied using radiation with any wavelength that is suitable for imaging a particular product structure.

Figure 8:
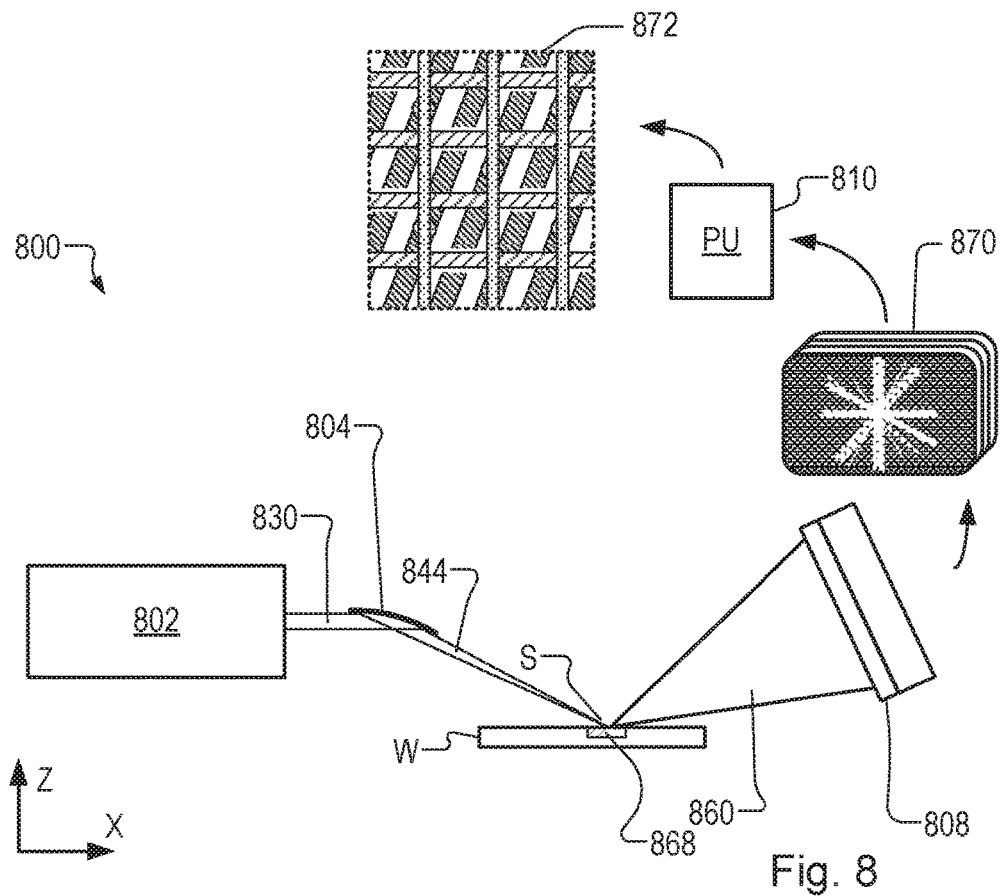
FIG. 8 illustrates schematically an inspection apparatus for obtaining data describing a three-dimensional product structure according to another embodiment of the invention.
Figure 9:
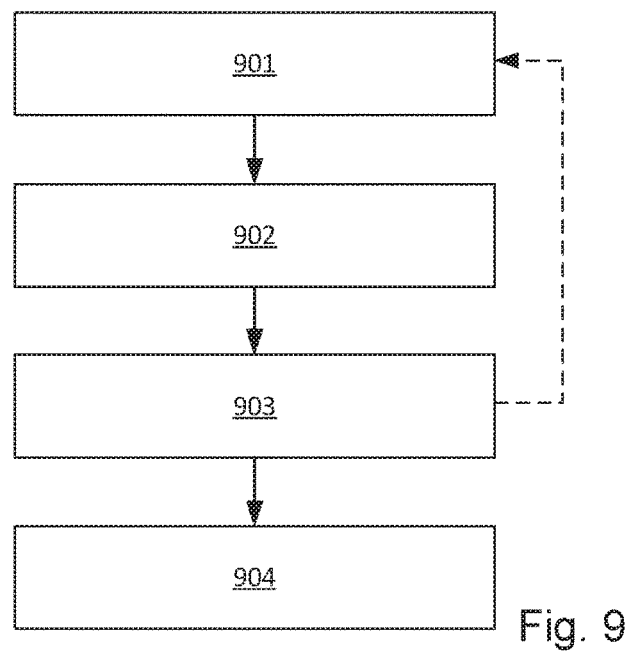
FIG. 9 illustrates a method for obtaining data describing a three-dimensional product structure using, for example, the apparatus of FIG. 8.

A further example of an apparatus and method for obtaining data describing a three-dimensional product structure will now be described with reference to FIGS. 8 and 9. This example uses an inspection apparatus substantially identical to that shown in FIG. 6 to perform the method. For ease of comparison with the schematic diagram of FIG. 6, some parts of the optical system 800 are labeled with reference signs similar to those used in FIG. 6, but with prefix "8" instead of "6". For this reason, only the elements of inspection apparatus 800 that differ from those of inspection apparatus 600 will be described in detail in the following.

The inspection apparatus 800 comprises a radiation source 802, such as an EUV radiation source. In this example, the radiation source is adapted to emit a only a single wavelength at any time, but to be tunable over a wavelength spectrum. This enables the wavelength of the radiation beam 830 to be varied over time so as to enable measurements to be carried out using different wavelengths.

In a first step 901, the radiation source 802 is adapted to output radiation at a specific wavelength. The wavelength may form part of a plurality of wavelengths. The plurality of wavelengths may for example be predetermined by a user or by a controlling entity, or it may be defined based on previous diffraction patterns. The plurality of wavelengths may be comprised within a specific wavelength spectrum.

In a second step 902, the product structure 868 is illuminated by focused beam of illuminating radiation 844, the illuminating radiation having a particular wavelength. In a third step 903, the detector 808 captures a diffraction pattern 870, as described above.

Steps 901-903 are repeated for each of the wavelengths in the plurality of wavelengths. In other terms, a separate diffraction pattern is captured for each of the plurality of wavelengths. Subsequently, the captured diffraction patterns 870 transmitted to a processing unit 810.

Figure 10:
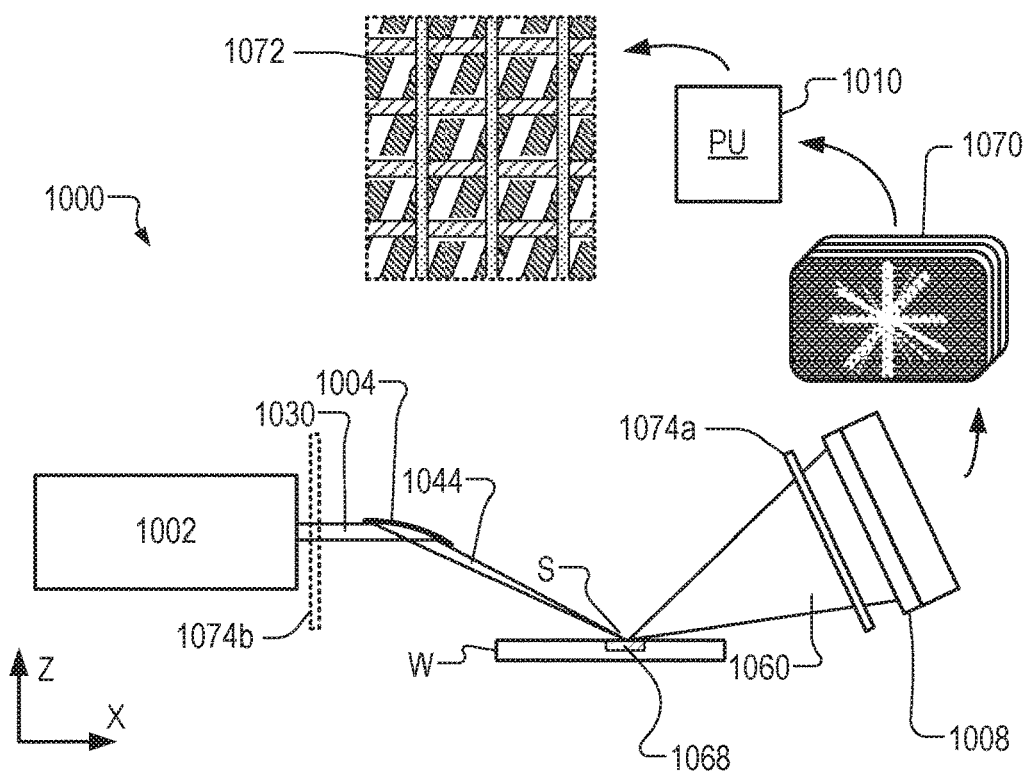
FIG. 10 illustrates schematically an inspection apparatus for obtaining data describing a three-dimensional product structure according to a further embodiment of the invention.
Figure 11:
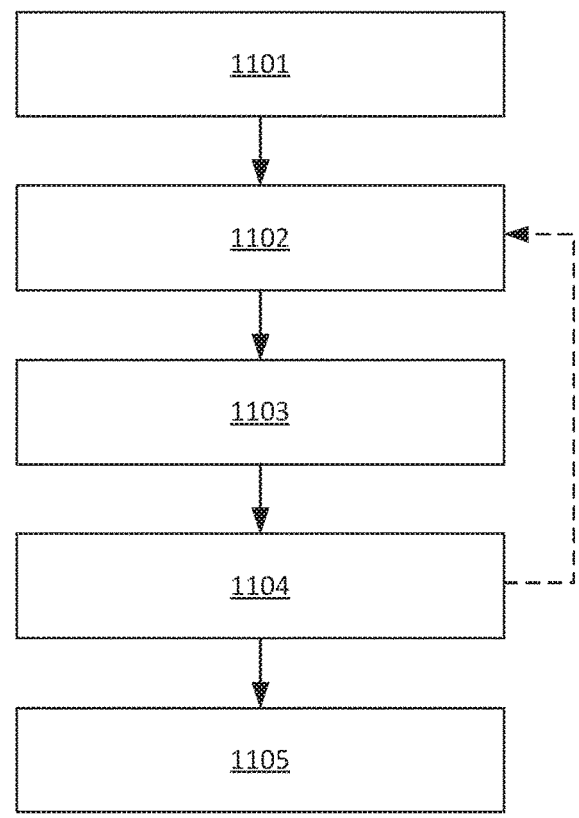
FIG. 11 illustrates a method for obtaining data describing a three-dimensional product structure using, for example, the apparatus of FIG. 10.

In a fourth step 904, the captured diffraction patterns 870 are used to reconstruct data describing the three-dimensional product structure as described with reference to FIGS. 6 and 7 above Another example of an inspection apparatus and method for obtaining data describing a three.dimensional product structure will now be described with reference to FIGS. 10 and 11. For ease of comparison with the schematic diagram of FIG. 6, some parts of the optical system 1000 are labeled with reference signs similar to those used in FIG. 6, but with prefix "10" instead of "6". For this reason, only the elements of inspection apparatus 1000 that differ from those of inspection apparatus 600 will be described in detail in the following.

In a first step 1101, the radiation source 1002 outputs a radiation beam 1030 with a first wavelength spectrum. The wavelength spectrum comprises a plurality of wavelengths.

The radiation beam propagates to illumination optical system 1004, which focuses the radiation beam into a focused beam of illuminating radiation 1044.

The inspection apparatus comprises an optical element, such as an optical filter, 1074. The optical element may in one example be positioned directly in front of the detector 1008 (indicated in FIG. 10 by reference numeral 1074*a*). Alternatively, the optical element may be positioned between the output of the radiation source 1002 and the illumination optical system 1004 (as indicated by reference numeral 1074*b* in FIG. 10). The optical element is configured to only let radiation with a specific wavelength pass and to block all other wavelengths (also referred to as a "band pass" filter). The pass wavelength of the optical element 1074 may be varied so as to allow the product structure to be illuminated with radiation having different wavelengths. In other terms, the optical element 1074 achieves the same effect as the tunable radiation source 802 in FIG. 8. The optical element 1074 may be implemented in any suitable fashion. For example, the optical element could without limitation comprise any of the following: a rapidly replaceable filter (for example a rotating filter wheel), a scanning monochromator, or an acousto-optic tunable filter.

In a second step 1102, the pass wavelength of the optical element is set to a first wavelength, the first wavelength being comprised in the plurality of wavelengths. Illuminating radiation with the first wavelength then illuminates the product structure 1068.

In a third step 1103, radiation 1060 that is scattered by product structure 1068 is filtered by the optical element 1074 before it arrives at the detector 1008. After being filtered, the filtered scattered radiation substantially comprises radiation having the first wavelength.

It will be appreciated that it is equally possible to perform the filtering step on the radiation beam 1030 or the focused beam of illuminating radiation 1044, rather than on the scattered radiation 1060. The choice of position for the optical element 1074 may be determined based on external factors, such as physical space requirements for the optical filter or other components of the inspection apparatus.

In a fourth step 1104, the scattered radiation is captured by a detector 1008. In the present example, the filtered scattered radiation will form a diffraction pattern 1070 on the surface of the detector.

Steps 1102-1104 are repeated for each of the wavelengths in the plurality of wavelengths so as to progressively capture one diffraction pattern at each of the wavelengths. In other terms, a separate diffraction pattern is captured for each wavelength in the plurality of wavelengths. Subsequently, the captured diffraction patterns are transmitted to a processing unit 1010.

In a fifth step 1105, the captured diffraction patterns 1070 are used to reconstruct data describing the three-dimensional product structure as described with reference to FIGS. 6 and 7 above.

Figure 12:
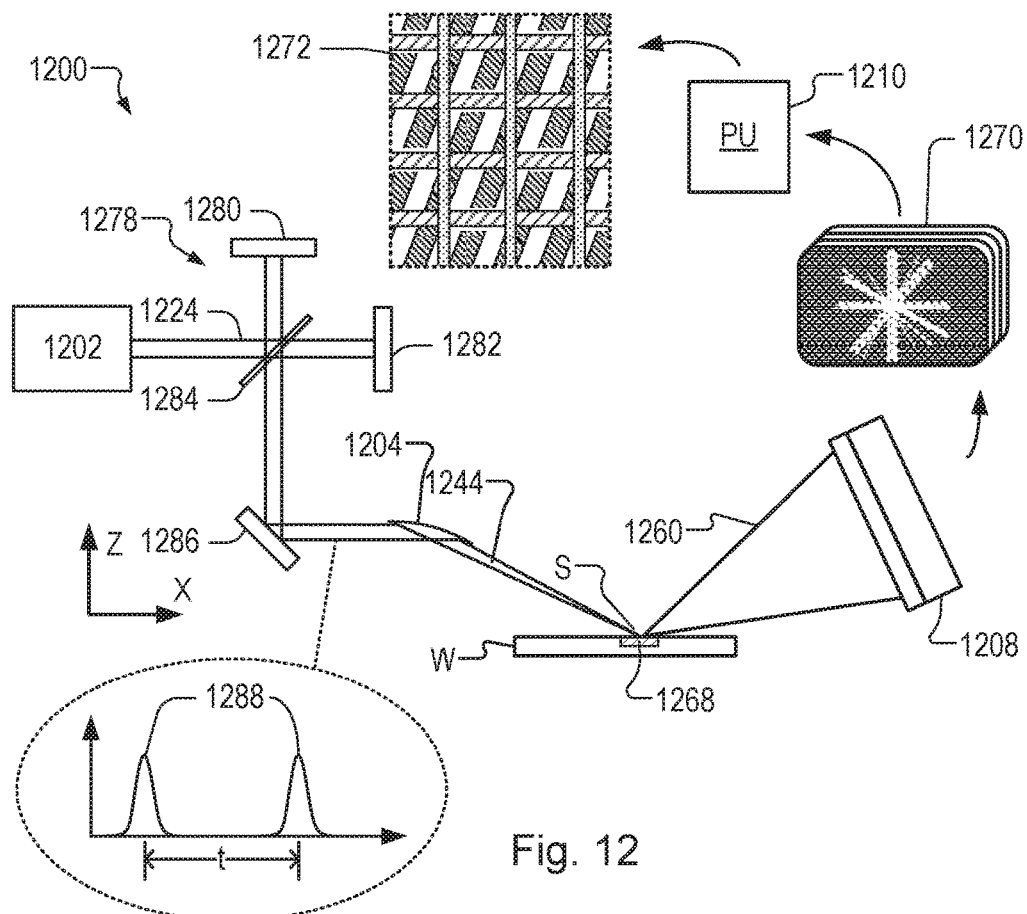
FIG. 12 illustrates schematically an inspection apparatus for obtaining data describing a three-dimensional product structure according to an embodiment of the invention.
Figure 13:
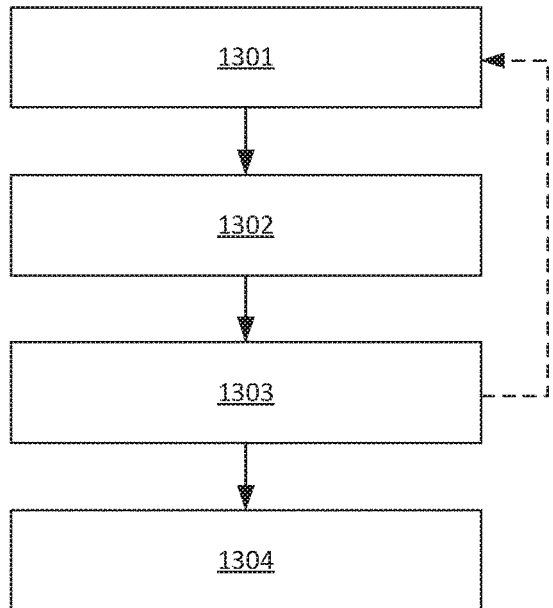
FIG. 13 illustrates a method for obtaining data describing a three-dimensional product structure using, for example, the apparatus of FIG. 12.

A further example of an inspection apparatus and method for obtaining data describing a three-dimensional product structure will now be described with reference to FIGS. 12 and 13. For ease of comparison with the schematic diagram of FIG. 6, some parts of the optical system 1200 are labeled with reference signs similar to those used in FIG. 6, but with prefix "12" instead of "6". For this reason, only the elements of inspection apparatus 1200 that differ from those of inspection apparatus 600 will be described in detail in the following.

The inspection apparatus, in this example, comprises a radiation source 1202 that emits radiation 1224 with a first wavelength spectrum, the wavelength spectrum comprising a plurality of wavelengths.

The inspection apparatus includes an interferometer 1278 that comprises a beamsplitter 1284, a fixed reflecting element 1280, and a movable reflecting element 1282. The interferometer is used in a known manner to generate first and second radiation pulses 1288, the pulses having a time delay t between them. The time delay t may be varied. In reality, instead of generating first and second radiation pulses, a plurality of pulses may be generated. Each pulse of the plurality may have a time delay between itself and the preceding pulse. The time delay between pulses may for example be incrementally varied between 0 and 200 fs (femtoseconds). In principle, any suitable time delay range could be used. In the following, reference will be made to first and second radiation pulses, although it will be appreciated that any two consecutive pulses of the plurality could be selected and used.

In a first step 1301, the product structure 1298 is illuminated with the first and second time-delayed radiation pulses 1288 that have a first time delay t. The first time delay t is comprised in a plurality of time delays. Individual time delay values to be used can be determined in any suitable fashion. In one example, the user may predefine the time delay values. In another example, the time delay values may be defined based on prior measurement data or on statistical data. In yet another example, the time delay values may be a series of incrementally increasing time delays.

In a second step 1302, first and second scattered radiation pulses 1260, which have been scattered by the product structure, are received at the detector 1208. From the first and second scattered radiation pulses, a diffraction pattern is then reconstructed.

In a third step 1303, the time delay t between the first and the second radiation pulses is changed to another time delay value comprised in the plurality of time delays.

Steps 1301-1303 are repeated for each of the time delays in the plurality of time delays to form a plurality of diffraction patterns 1270. The diffraction patterns are subsequently transmitted to the processing unit 1210.

In a fourth step 1304, data describing the three-dimensional product-structure 1272 is reconstructed based on the plurality of diffraction patterns 1270 in a similar manner to that described with reference to FIGS. 6 and 7 above.

In association with the optical system hardware, an embodiment may include a computer program containing one or more sequences of machine-readable instructions defining methods of reconstructing diffracting patterns and/or data describing three-dimensional product structures, as well as controlling the inspection apparatus 400 to implement the illumination modes and other aspects of those metrology recipes. This computer program may be executed for example in a separate computer system employed for the image calculation/control process. Alternatively, the calculation steps may be wholly or partly performed within processing unit PU in the apparatus of FIG. 4, 6, 8, 10 or 12 and/or the control unit LACU of FIGS. 1 and 2. There may also be provided a data storage medium (e.g., semiconductor memory, magnetic or optical disk) having such a computer program stored therein.

Although specific reference may have been made above to the use of embodiments of the invention in the context of optical lithography, it will be appreciated that the invention may be used in other applications, for example imprint lithography. In imprint lithography, topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the invention are provided in below numbered clauses:

1. A method of obtaining data describing a three-dimensional product structure, the method comprising the steps of:
    (a) illuminating the three-dimensional product structure with illuminating radiation, the illuminating radiation having at least one controllable characteristic;
    (b) capturing a plurality of diffraction patterns formed by said radiation after scattering by the three-dimensional product structure, wherein each diffraction pattern is formed by illuminating radiation, the illuminating radiation having a specific value of the at least one characteristic; and
    (c) reconstructing the data describing the three-dimensional product structure based on the captured plurality of diffraction patterns.

2. A method according to clause 1, wherein the step of reconstructing comprises performing phase retrieval on the captured diffraction patterns.

3. A method according to clause 1 or 2, wherein the illuminating radiation comprises radiation with a first wavelength spectrum, the first wavelength spectrum comprising a first plurality of wavelengths.

4. A method according to clause 3, wherein the step of capturing comprises using an optical element to progressively capture one diffraction pattern of the plurality of diffraction patterns at each of the wavelengths of the first plurality of wavelengths.

5. A method according to clause 4, wherein the optical element comprises at least one of: a rotating filter wheel, a scanning monochromator, or an acousto-optic filter.

6. A method according to clause 3, wherein the step of illuminating comprises providing first and second coherent radiation pulses, the second radiation pulse having one of a plurality of time delays, and wherein
    the step of capturing comprises:
    (i) receiving first and second scattered radiation pulses formed by the first and second coherent radiation pulses after scattering by the product surface;
    (ii) reconstructing a diffraction pattern based on the first and second scattered radiation pulses; and
    repeating steps (i) and (ii) for each time delay in the plurality of time delays.

7. A method according to clause 1 or 2, wherein the step of illuminating comprises adapting a radiation source to output illuminating radiation having a single wavelength, and further comprising repeating steps (a), and (b) for each wavelength in a second plurality of wavelengths.

8. A method according to any previous clause, further comprising reconstructing a three-dimensional image of the three-dimensional product structure based on the data.

9. An inspection apparatus comprising means for carrying out the method of any of clauses 1 to 8.

10. An inspection apparatus according to clause 9, further comprising:
    an illumination optical system operable to illuminate a three-dimensional product structure on a substrate with illuminating radiation, the illuminating radiation having at least one controllable characteristic;
    a detector operable to capture a plurality of diffraction patterns formed by said radiation after scattering by the three-dimensional product structure, each diffraction pattern being formed by illuminating radiation having a specific value of the at least one controllable characteristic; and a processing unit operable to reconstruct data describing the three-dimensional product structure based on the captured plurality of diffraction patterns.

11. An inspection apparatus according to clause 10, wherein the processing unit is operable to perform phase retrieval on the captured diffraction patterns.

12. An inspection apparatus according to clause 10 or 11, wherein the illuminating radiation comprises radiation with a first wavelength spectrum, the first wavelength spectrum comprising a plurality of wavelengths.

13. An inspection apparatus according to clause 12, further comprising an optical element operable to progressively capture each diffraction pattern at one of the wavelengths of the plurality of wavelengths.

14. An inspection apparatus according to clause 13, wherein the optical element comprises at least one of: a rotating filter wheel, a scanning monochromator, or an acousto-optic filter.

15. An inspection apparatus according to clause 12, wherein the illumination optical system is further operable to provide first and second coherent radiation pulses, the second radiation pulse having one of a plurality of time delays, and wherein:

the detector is further operable to
(i) receive first and second scattered radiation pulses formed by the first and second coherent radiation pulses after scattering by the product surface;
the processing unit is further operable to
(ii) reconstruct a diffraction pattern based on the first and second scattered radiation pulses; and
repeating steps (i) and (ii) for each time delay in the plurality of time delays.

16. An inspection apparatus according any of clauses 9-11, wherein the illumination optical system comprises a radiation source, the radiation source being adaptable to output illuminating radiation having a single wavelength, and
wherein both the illumination optical system and the detector are operable to respectively illuminate the three-dimensional product structure and capture a plurality of diffraction patterns for each wavelength in a second plurality of wavelengths.

17. An inspection apparatus according to any of clauses 9-16, wherein the processing unit is further operable to reconstruct a three-dimensional image of the product structure.

18. A lithographic apparatus comprising an inspection apparatus according to any of clauses 9-17.

19. A method of manufacturing devices wherein device features and metrology targets are formed on a series of substrates by a lithographic process, wherein properties of the metrology targets on one or more processed substrates are measured by a method described in any of clauses 1 to 8, and wherein the measured properties are used to adjust parameters of the lithographic process for the processing of further substrates.

20. A computer program product comprising machine-readable instructions for causing a processor to perform the reconstructing step (c) of a method described in any of clauses 1 to 8.

21. A computer program product according to clause 20, further comprising instructions for causing a processor to perform the reconstructing step (i) of a method described in clause 6.

22. A lithographic system comprising:
a lithographic apparatus comprising:
an illumination optical system arranged to illuminate a pattern,
a projection optical system arranged to project an image of the pattern onto a substrate; and
an inspection apparatus according to any of clauses 8 to 17,
wherein the lithographic apparatus is arranged to use one or more parameters calculated by the inspection apparatus in applying the pattern to further substrates.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of obtaining data describing a three-dimensional product structure, the method comprising:
illuminating the three-dimensional product structure with illuminating radiation, the illuminating radiation having at least one controllable characteristic;
capturing a plurality of diffraction patterns formed by said radiation after scattering by the three-dimensional product structure, wherein each diffraction pattern is formed by illuminating radiation, the illuminating radiation having a specific value of the at least one controllable characteristic; and
reconstructing the data describing the three-dimensional product structure based on the captured plurality of diffraction patterns.

2. The method of claim 1, wherein the reconstructing comprises performing phase retrieval on the captured diffraction patterns.

3. The method of claim 1, wherein the illuminating radiation comprises radiation with a first wavelength spectrum, the first wavelength spectrum comprising a first plurality of wavelengths.

4. The method of claim 3, wherein the capturing comprises using an optical element to progressively capture one diffraction pattern of the plurality of diffraction patterns at each of the wavelengths of the first plurality of wavelengths.

5. The method of claim 4, wherein the optical element comprises a rotating filter wheel, a scanning monochromator, or an acousto-optic filter.

6. The method of claim 3, wherein:
the illuminating comprises providing first and second coherent radiation pulses, the second radiation pulse having one of a plurality of time delays, and the capturing comprises:
  receiving first and second scattered radiation pulses formed by the first and second coherent radiation pulses after scattering by the product surface;
  reconstructing a diffraction pattern based on the first and second scattered radiation pulses; and
  repeating the receiving and reconstructing for each time delay in the plurality of time delays.

7. The method of claim 1, wherein the illuminating comprises adapting a radiation source to output illuminating radiation having a single wavelength,
  and further comprising repeating the illuminating and capturing for each wavelength in a second plurality of wavelengths.

8. The method of claim 1, further comprising reconstructing a three-dimensional image of the three-dimensional product structure based on the data.

9. An inspection apparatus comprising:
  an illuminator configured to illuminate a three-dimensional product structure with illuminating radiation, the illuminating radiation having at least one controllable characteristic;
  a sensor configured to capture a plurality of diffraction patterns formed by said radiation after scattering by the three-dimensional product structure, wherein each diffraction pattern is formed by illuminating radiation, the illuminating radiation having a specific value of the at least one controllable characteristic; and
  a reconstruction device configured to reconstruct the data describing the three-dimensional product structure based on the captured plurality of diffraction patterns.

10. A method of manufacturing devices wherein device features and metrology targets are formed on a series of substrates by a lithographic process, wherein properties of the metrology targets on one or more processed substrates are measured by a method comprising:
  illuminating a three-dimensional product structure with illuminating radiation, the illuminating radiation having at least one controllable characteristic;
  capturing a plurality of diffraction patterns formed by said radiation after scattering by the three-dimensional product structure, wherein each diffraction pattern is formed by illuminating radiation, the illuminating radiation having a specific value of the at least one controllable characteristic;
  reconstructing the data describing the three-dimensional product structure based on the captured plurality of diffraction patterns; and
  using the measured properties to adjust parameters of the lithographic process for the processing of further substrates.

11. A computer program product comprising machine-readable instructions for causing a processor to perform operations comprising:
  illuminating a three-dimensional product structure with illuminating radiation, the illuminating radiation having at least one controllable characteristic;
  capturing a plurality of diffraction patterns formed by said radiation after scattering by the three-dimensional product structure, wherein each diffraction pattern is formed by illuminating radiation, the illuminating radiation having a specific value of the at least one controllable characteristic;
  reconstructing the data describing the three-dimensional product structure based on the captured plurality of diffraction patterns.

12. The computer program product of claim 11, further comprising instructions for causing a processor to reconstruct a diffraction pattern based on the first and second scattered radiation pulses.

* * * * *